US010980717B2

United States Patent
Lee et al.

(10) Patent No.: US 10,980,717 B2
(45) Date of Patent: Apr. 20, 2021

(54) AQUEOUS PERFUME COMPOSITIONS

(71) Applicant: ELC Management LLC, Melville, NY (US)

(72) Inventors: Wilson A. Lee, Hauppauge, NY (US); Natalie M. Drucker, Long Island City, NY (US)

(73) Assignee: ELC Management LLC, Melville, NY (US)

( * ) Notice: Subject to any disclaimer, the term of this patent is extended or adjusted under 35 U.S.C. 154(b) by 185 days.

(21) Appl. No.: 16/267,441

(22) Filed: Feb. 5, 2019

(65) Prior Publication Data
US 2020/0246227 A1    Aug. 6, 2020

(51) Int. Cl.
| | | |
|---|---|---|
| *A61K 8/06* | (2006.01) | |
| *A61K 8/81* | (2006.01) | |
| *A61K 8/34* | (2006.01) | |
| *A61Q 13/00* | (2006.01) | |

(52) U.S. Cl.
CPC ............... *A61K 8/062* (2013.01); *A61K 8/068* (2013.01); *A61K 8/8135* (2013.01); *A61K 8/8152* (2013.01); *A61Q 13/00* (2013.01); *A61K 8/345* (2013.01)

(58) Field of Classification Search
None
See application file for complete search history.

(56) References Cited

U.S. PATENT DOCUMENTS

| | | | |
|---|---|---|---|
| 4,803,195 A | 2/1989 | Holzner | |
| 5,374,614 A | 12/1994 | Behan | |
| 6,403,109 B1* | 6/2002 | Stora | A61K 8/06 424/401 |
| 6,774,101 B2 | 8/2004 | Stora et al. | |
| 7,226,901 B2 | 6/2007 | Stora | |
| 7,655,613 B2 | 2/2010 | Vlad et al. | |
| 7,846,889 B2 | 12/2010 | Vlad et al. | |
| 8,343,521 B2 | 1/2013 | Shick et al. | |
| 9,107,841 B2* | 8/2015 | Balcke | A61K 8/35 |
| 9,301,910 B2 | 4/2016 | Yontz | |
| 2003/0186836 A1 | 10/2003 | Dumanois et al. | |
| 2004/0209795 A1 | 10/2004 | Vlad | |
| 2005/0053567 A1 | 3/2005 | Liu | |
| 2005/0064000 A1* | 3/2005 | Kropke | A61K 8/922 424/401 |
| 2011/0073126 A1 | 3/2011 | Mu et al. | |
| 2016/0338915 A1* | 11/2016 | Shavit | A61K 8/731 |

* cited by examiner

*Primary Examiner* — Bethany P Barham
*Assistant Examiner* — Peter Anthopolos
(74) *Attorney, Agent, or Firm* — Peter Giancana

(57) ABSTRACT

Reduced-ethanol perfume compositions according to the invention comprise specific combinations of acrylates/VA copolymer and acrylates copolymer in an aqueous base or delivery vehicle. The perfume compositions according to the invention are easy to manufacture and provide an aqueous perfume composition that preserves aromatic integrity (intensity, duration and range), even in emulsion form. The most advantageous use of compositions of the invention are as parfums, eau de parfums, eau de toilettes, and colognes. However, the invention may also find use in many types of fragranced products, such as those used on the skin and hair of humans or animals, in cleaning products of all types, in air deodorizers, air fresheners, and more.

6 Claims, No Drawings

AQUEOUS PERFUME COMPOSITIONS

FIELD OF THE INVENTION

The present invention is in the field of fragrance compositions, and more specifically relates to liquid, aqueous perfume compositions.

BACKGROUND

The overwhelming majority of liquid perfume compositions use alcohol, typically ethanol, as a solubilizer for aromatic ingredients that are usually included in the composition in the form of fragrant oils. Products with concentrations of ethanol between 50 and 95% by volume are common. The use of ethanol solubilizer renders a transparent perfume composition. Nevertheless, the use of ethanol has its drawbacks. These include, but are not be limited to, acute contact dermatitis. Furthermore, ethanol is classified as a volatile organic compound (VOC). For some time, there has been an effort to reduce the level of VOC's in the ambient environment. Other drawbacks are apparent in cultures where the use of alcohol is strictly regulated or prohibited on religious grounds.

There have been efforts to reduce or eliminate alcohol from perfume products. For example, water-based perfume products are known, but these have not gained widespread acceptance for reasons related to performance and aesthetics. One problem is that perfuming ingredients tend to be insoluble in water due to their hydrophobic nature. Attempts to address this by forming emulsion compositions have been tried. See, for example, U.S. Pat. Nos. 4,803,195; 5,374,614; 6,403,109; 6,774,101; US2003/0186836; US2004/0209795; U.S. Pat. Nos. 7,226,901; 7,655,613; 7,846,889; 8,343,521; 9,301,910. However, many emulsion perfume compositions have their own drawbacks. For example, the use of too much surfactant can lead to skin irritation, a tacky feel, and alter the perception of the aromatic ingredients. This is especially true for microemulsion compositions, which use a relatively high concentration of surfactant, but macroemulsions and nanoemulsions may also suffer from the same problem. As a result, water-based perfume compositions have, in general, not provided the same intensity, duration and range as traditional ethanol based fragrances. Regarding loss of intensity, we mean that the aroma of a water-based fragrance tends to be less potent, than a traditional perfume. Regarding decreased duration, we mean that water-based perfume compositions are perceptible to the human nose for a significantly shorter time than a traditional ethanol-based perfume composition. Range, as used herein, is sometimes referred to as olfactive linearity. Regarding loss of range, we mean that following application to the skin or other surface, the blend of aromatic notes given off by aqueous-based perfume compositions is not maintained, even when some fragrance is still perceptible. Thus, there is still a need for an aqueous-based perfume composition having comparatively little ethanol, yet preserving aromatic integrity (intensity, duration and range). The present invention provides such compositions in emulsion form. To the best of our knowledge, the prior art does not disclose or suggest the compositions of present invention, specifically water-based perfume compositions comprising 4.5% to 18.5% of acrylates/ VA copolymer and 0.25% to 1.0% of acrylates copolymer by weight, as disclosed herein. Nor does it disclose ratios of these materials as disclosed herein, nor their usefulness in preserving the performance of perfume compositions.

SUMMARY

Reduced-ethanol perfume compositions according to the invention comprise specific combinations of acrylates/VA copolymer and acrylates copolymer in an aqueous base or delivery vehicle. The perfume compositions according to the invention are easy to manufacture and provide an aqueous perfume composition that preserves aromatic integrity (intensity, duration and range), even in emulsion form. The most advantageous use of compositions of the invention are as parfums, eau de parfums, eau de toilettes, and colognes. However, the invention may also find use in many types of fragranced products, such as those used on the skin and hair of humans or animals, in cleaning products of all types, in air deodorizers, air fresheners, and more.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

Throughout the present specification, "film former" or the like refers to a polymer that leaves a film on the substrate to which it is applied, for example, after a solvent accompanying the film former has evaporated, absorbed into and/or dissipated on the substrate.

"Comprise" means that a list of elements may not be limited to those explicitly recited.

By "emulsion" we mean a stable dispersion of a discontinuous (or internal) phase in a continuous (or external) phase (oil in water or water in oil), facilitated by one or more surfactants. For clarity, we provide definitions of three main types of emulsions that are common in the personal care field.

A macroemulsion (usually called simply an "emulsion") is an anisotropic, two-phase system that is kinetically stable, but thermodynamically unstable, which means they require high energy input for the formation of droplets that disperse in the continuous phase. Regarding the characteristic sizes of the droplets in the internal phase, the literature proposes many definitions. The International Union of Pure and Applied Chemistry (IUPAC) recommends 10 nm-100 μm. These droplet structures naturally degrade with time by coalescing and separating from the continuous phase, but surfactants, which decrease surface tension at the oil-water interface, can lengthen the life of a macroemulsion.

Microemulsions (sometimes called micellar emulsions) are significantly different from macroemulsions. Microemulsions are isotropic, one-phase systems of water, oil and relatively high concentrations of surfactants. Microemulsions are thermodynamically stable, which means that they form spontaneously with simple, low energy mixing. Internal phase structures are dynamic, constantly changing shape, but the range of sizes is typically about 1 nm-100 nm (IUPAC). Owing to this small particle size, microemulsions are generally translucent.

Still different are nanoemulsions (also known as miniemulsions or submicron emulsions). Like macroemulsions, nanoemulsions are two-phase systems in which droplets of the discontinuous phase are dispersed in the continuous phase. However, the mean droplet size of nanoemulsions can range from 50 nm to 1000 nm (IUPAC) in diameter. Nanoemulsions at the lower end of this range are translucent, because the droplet size is below the wavelength of visible light. Nanoemulsions are kinematically stable, but thermodynamically unstable, and must be held together by surfactants. They may be formed by high-energy emulsification methods, such as shearing with a homogenizer or ultrasound. Alternatively, phase inversion methods exist which require very little energy.

Water

Compositions of the invention comprise water, typically from 30% to 70% of water by weight of the total composition, while 50% to 60% is expected to be common. This amount of water is that from all sources, such as that in Vinysol 2140L and Daitosol 5000AD, discussed below.

Acrylates/VA Copolymer

A main ingredient of the invention is acrylates/VA copolymer (INCI name), $C_{15}H_{26}O_4$, also known as ethenyl acetate or 2-ethylhexyl prop-2-enoate (IUPAC names); CAS number 25067-02-1. For detailed information, see PubChem Compound Database; CID=168269.

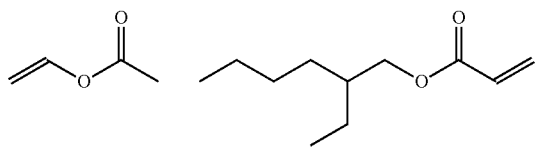

In cosmetics, this material often functions as a binder, film former, adhesive and/or hair fixative. When deployed in aqueous cosmetic systems acrylates/VA copolymer can impart a film on the skin or hair. The pure acrylates/VA copolymer film features a temperature dependence, such that a water rinse of about 40° C. or more will degrade the film, and allow it to be removed from a surface, while retaining its integrity at temperatures at or below normal skin temperature (i.e. 36.5-37.5° C.).

Perfume compositions of the invention typically comprise 4.5% to 18.5% of acrylates/VA copolymer by total weight of the composition, for example 7% to 16%, for example 9% to 14% by total weight of the composition.

Acrylates/VA copolymer is commercially available, for example, as Vinysol 2140L from Daido Chemical Corp. Vinysol 2140L is a 46.6% aqueous mixture of acrylates/VA copolymer. Therefore, when using Vinysol 2140L, in order to achieve the concentrations of acrylates/VA copolymer noted above, the concentration of Vinysol 2140L should be about 10% to 40%, for example 15%-35%, for example 20%-30% by total weight of the composition. Vinysol 2140L is reported to have a pH of 4.5, a viscosity of 2,000 mPa-s, a calculated glass transition temperature ($T_g$) of −9° C., while the film exhibits a break elongation of 1,200%, and a break strength of 1.2 MPa (when spread to a thickness 0.1 mm).

Acrylates Copolymer

Another main ingredient of the invention is an acrylates polymer that has a lower $T_g$ than acrylates/VA copolymer. In general, a lower $T_g$ provides more flexibility to the resulting film. In the present invention, a second main ingredient is acrylates copolymer, $C_{14}H_{22}O_6$, also known as ethyl prop-2-enoate; methyl 2-methylprop-2-enoate or 2-methylprop-2-enoic acid (IUPAC names); CAS number 25133-97-5. For detailed information, see PubChem Compound Database; CID=168299. In various types of cosmetic formulations, acrylates copolymer has a wide variety of uses including as film formers, hair fixatives, binders, and suspending agents, viscosity enhancers, antistatic agents and adhesives. At concentrations discussed herein, the combination of acrylates/VA copolymer and acrylates copolymer form a useful water-soluble complex that dries to a hydrophobic film when applied to a surface.

In the present invention, useful concentrations of acrylates copolymer are from 0.25% to 1.0% based on total weight of the composition; for example 0.35% to 0.8%, or, for example 0.5% to 0.7%. Additionally, we have noted particularly good results when the weight ratio of acrylates/VA copolymer to acrylates copolymer is in the range of 10:1 to 30:1, preferably from 15:1 to 25:1, and more preferably about 20:1.

Acrylates copolymer is commercially available, for example, as Daitosol 5000AD from Daito Kasei Kogyo Co. Daitosol 5000AD is a 50% aqueous mixture of acrylates copolymer. Therefore, in order to achieve the concentrations of acrylates copolymer noted above, the concentration of Daitosol 5000AD should be about 0.5% to 2%, for example 0.7% to 1.6%, for example 1.0% to 1.4% by total weight of the composition. Daitosol 5000AD is reported to have a pH of 5.5-7.5, a viscosity of 50-100 mPa-s, a glass transition temperature ($T_g$) of about −14° C.

Plasticizer

While it is possible to formulate an aqueous perfume composition according to the invention without further modification to the acrylates/VA copolymer—acrylates copolymer complex, preferred compositions may comprise one or more materials in the aqueous phase that are able to plasticize the acrylates/VA copolymer. Such plasticizers will lower the freezing point of the final composition to a temperature that is suitable for commercial distribution and consumer use. Furthermore, such plasticizers will modify the porosity of the film that results from the acrylates/VA copolymer—acrylates copolymer complex, when the perfume composition is applied to a surface. In general, over the ranges contemplated herein, more plasticizer in the aqueous phase tends to increase the size of the surface pores that are present in the acrylates/VA copolymer—acrylates copolymer film. Controlling this pore size is key to controlling the release of fragrance as a function of time, and maintaining the integrity of the perfuming ingredients in the composition. In each specific composition, routine experimentation may suggest the optimum amount of plasticizer. However, for guidance, we have found that a weight ratio of acrylates/VA copolymer to plasticizer of about 1:1 gives excellent results. We note that less plasticizer may also give useful results, such as 5:1, or even 10:1 by weight of acrylates/VA copolymer to plasticizer. Since the concentration of acrylates/VA copolymer is 4.5% to 18.5% by weight, total plasticizer will not exceed about 4.5% by weight of the total composition.

Useful plasticizers include glycols, also known as diols (chemical compounds comprising two hydroxyl groups). Potentially suitable glycols include butanediols, propanediols and pentylene glycols. Preferred is 1,3-propanediol.

Other useful plasticizers are simple cosmetic grade alcohols (for example, ethanol or isopropyl alcohol) in amounts up to about 5% by weight of the final composition. While an alcohol-free composition is most preferred, 5% is a substantial reduction from the amount typically found in conventional fragrance compositions. Glycol or alcohol may be used alone or in combination, the total being consistent with the weight ratios of acrylates/VA copolymer to plasticizer described above.

Aromatic Ingredients

Aromatic ingredients include one or more essential oils, distillates, extracts, synthetics, and other ingredients added for the sole purpose of imparting an odor or scent, or to counteract an odor. Depending on the type of perfumed product, the level of aromatic ingredients, will typically vary from about 3% to about 30% by weight of the final perfume composition. Most aromatic ingredients are hydrophobic, and will form part or all of the oil phase. Essential oils are pure distillations of flowers, herbs, roots, or resins, whereas "fragrance oil" usually refers to either blends of synthetic aromatic ingredients or blends of essential oils cut with a carrier oil. For example, one or more essential oils or one or more fragrance oils, or a combination of these may form most or all of the oil phase. Or the oil phase may comprise other aromatic ingredients dispersed in a cosmetically acceptable oil.

Other Ingredients

The perfume compositions may also comprise preservatives as needed, typically up to about 2% by weight of the composition. Also, viscosity modifiers, and/or pH adjusters may be used as needed to create a consumer acceptable product, typically at levels of less than 1% by weight of the composition. At these levels, preservatives, viscosity modifiers and pH adjusters do not seem to adversely affect the aromatic integrity of the perfume compositions. Compositions comprise no more than 5% alcohol by weight, preferably less than 3%, more preferably, no alcohol.

Form of the Perfume Compositions

Preferred liquid perfume compositions of the invention have a watery consistency, and are suitable for dispensing from a mechanical spray pump or aerosolizer. The compositions are oil-in-water emulsions, but unlike previous water-based perfume products, the compositions disclosed herein are able to utilize much less emulsifier and/or surfactant, which greatly, if not totally negates the problems introduced by the use of high levels of these ingredients. Based on the total weight of the composition, it is preferable if the perfume composition comprises no more than 5% by weight of surfactants and/or emulsifiers, more preferably less than 3%, still more preferably less than 1%. Example 1 shows an effective oil-in-water macroemulsion composition of the invention. Phase 1 is the continuous aqueous phase. Phase 2 is the discontinuous oil phase. In this example, and preferably, the acrylates/VA copolymer and acrylates copolymer are added after the emulsion is formed. However, an effective composition is also achieved if the are added to the aqueous phase.

Example 1

| Phase | Ingredient | wt % Concentration |
|---|---|---|
| 1 | water | 49.47 |
| 1 | SD alcohol | 3.72 |
| 1 | hydrogenated lecithin (surfactant) | 0.60 |
| 1 | caustic soda 30% | 0.25 |
| 1 | polyglyceryl-3 disiloxane dimethicone (emulsifier) | 0.96 |
| 1 | propanediol | 4.00 |
| 1 | phenoxyethanol | 0.25 |
| 2 | fragrance oil | 15.00 |

Example 1 -continued

| Phase | Ingredient | wt % Concentration |
|---|---|---|
| 3 | [1]xanthan gum premix | 10.00 |
| 4 | [2]Vinysol 2140L | 15.00 |
| 4 | [3]Daitosol 5000AD | 0.75 |

[1]water 96.70%/xanthan gum 3.10%/preservatives 0.20%.
[2]46.6% aqueous mixture of acrylates/VA copolymer.
[3]50% aqueous mixture of acrylates copolymer.

The composition uses a cold mixing process, as follows:
1. Premix xanthan gum stage in a suitable beaker with homogenizer until uniform.
2. In a main beaker add sequence 1 ingredients in the order listed, with homogenizer speed set on 10.
3. After all the sequence 1 are in the main beaker mix for additional 10 minutes.
4. Add Sequence 2 to the main beaker with homogenizer speed set at 30.
5. Mix for 30 minutes.
6. Add Sequence 3 at homogenizer speed 30.
7. Add Sequence 4 with same homogenizer speed 30.
8. Mix additional 30 minutes.

Fragrance Integrity Study

An eight hour study was conducted to investigate the ability of a composition according to the present invention to maintain fragrance integrity. Two samples were analyzed and compared, a test formula according to Example 1 above, and a control. The control was the same fragrance oil used in the test formula. Gas Chromatography and Mass Spectrometry (GC/MS) were utilized to determine the overall volatile fingerprint, and to identify compounds being given off by test samples at various intervals.

Samples for analysis were initially prepared on slides. In order to maintain the same concentration of fragrance oil in the test samples and the control, the weights of the control and test samples were adjusted. Approximately 0.09 g of the control, and 0.60 g of test sample were weighed onto individual glass slides. The samples were uniformly spread on the slides, then placed on a 32° C. hot plate, to dry. Samples were prepared with drying times of 2, 4, 6 and 8 hours, as well as initial. After the allotted drying time, each slide was placed in a 50 mL flat test tube, to which 10 mL isopropyl alcohol was added via volumetric pipette. The test tube preparations were then sonicated for two 15 minute intervals, and vortexed, in order to remove all of the dried formulation from the slide. When each preparation was observed to completely enter solution, each sample was filtered through 0.45 um PTFE filters, and analyzed on the GC/MS.

Chromatographic Profiles

Evaluation of the chromatographic profiles of the control samples indicates a significant decrease in the overall concentration of the total volatile compounds over the eight hour time period. In contrast, evaluation of the chromatographic profiles of the test samples, indicates that the volatile aromatic ingredients of the formulation were retained over the eight hour time period.

Area Count Quantitation

In order to represent the amount of volatile compounds retained by the control samples and the test samples, area counts of the following four key aromatic ingredients were recorded: limonene, linalool, vetiverol and geranyl acetate.

A. CONTROL SAMPLE RESULTS

At the two hour time point, limonene, linalool and vetiverol were below the detection limit. Geranyl acetate was retained at 49%.

At the four hour time point, only geranyl acetate retained, at 5%.

At the six and eight hour time points, all four key volatile compounds were below detection limit.

B. TEST SAMPLE RESULTS

At the two hour time point, all four compounds were retained in the test samples; limonene, linalool, vetiverol and geranyl acetate were retained at 53%, 58%, 78% and 89%, respectively.

At the four hour time point limonene, linalool, vetiverol and geranyl acetate were present at 41%, 44%, 68% and 81%, respectively.

At the eight hour time point, limonene, linalool, vetiverol and geranyl acetate were present at 32%, 40%, 64% and 78%, respectively.

C. CONCLUSION

Over an eight hour time period, the chromatographic profiles and area counts obtained, show that the test samples retained a significant amount of the aromatic ingredients, when compared to the control. Significant intensity was still present at the end of the 8 hour test period, which duration is suitable for consumer use. Also, the range of aromatic notes (olfactive linearity) was fully maintained. We suspect that volatile aromatic ingredients are being retained on the surface of the acrylates/VA copolymer and/or acrylates copolymer, and volatilizing more slowly than other water based fragrance compositions.

What is claimed is:

1. An oil-in-water macroemulsion composition comprising:
    an aqueous phase that comprises, by total weight of the composition:
        30% to 70% of water;
        4.5% to 18.5% of acrylates/VA copolymer;
        0.25% to 1.0% of acrylates copolymer;
        1,3-propanediol, wherein the ratio by weight of acrylates/VA copolymer to 1,3-propanediol ranges from 1:1 to 10:1;
    an oil phase that comprises 3% to 30% of essential oils by total weight of the composition; and
    no more than 3% of surfactants and/or emulsifiers.

2. The composition of claim 1 wherein the ratio by weight of acrylates/VA copolymer to acrylates copolymer is 10:1 to 30:1.

3. The composition of claim 1 wherein the ratio by weight of acrylates/VA copolymer to acrylates copolymer is 15:1 to 25:1.

4. The composition of claim 1 further comprising one or more aromatic distillates, aromatic extracts, and aromatic synthetics.

5. The composition of claim 1 further comprising one or more alcohols.

6. The composition of claim 1 comprising no more than 5% alcohol by total weight of the composition.

* * * * *